(12) United States Patent
John et al.

(10) Patent No.: US 8,005,283 B2
(45) Date of Patent: Aug. 23, 2011

(54) METHOD AND DEVICE FOR THE COMBINED REPRESENTATION OF 2D FLUOROSCOPIC IMAGES AND A STATIC 3D IMAGE DATA SET

(75) Inventors: Matthias John, Nürnberg (DE); Andreas Meyer, Möhrendorf (DE); Marcus Pfister, Bubenreuth (DE); Norbert Rahn, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 1005 days.

(21) Appl. No.: 11/903,537

(22) Filed: Sep. 21, 2007

(65) Prior Publication Data

US 2008/0175455 A1    Jul. 24, 2008

(30) Foreign Application Priority Data

Sep. 29, 2006   (DE) .......................... 10 2006 046 733

(51) Int. Cl.
*G06K 9/00*   (2006.01)
(52) U.S. Cl. .......................... 382/130; 382/128; 382/154
(58) Field of Classification Search .................. 382/128, 382/131, 132, 154; 600/424, 428, 407, 425; 345/420; 378/62, 63
See application file for complete search history.

(56) References Cited

U.S. PATENT DOCUMENTS

| | | | | |
|---|---|---|---|---|
| 7,227,923 | B2* | 6/2007 | Edic et al. .......................... | 378/9 |
| 7,689,019 | B2* | 3/2010 | Boese et al. .................. | 382/128 |
| 7,801,342 | B2* | 9/2010 | Boese et al. .................. | 382/128 |
| 7,873,403 | B2* | 1/2011 | Lachner et al. ............... | 600/425 |
| 2002/0049375 | A1* | 4/2002 | Strommer et al. ............ | 600/407 |
| 2003/0181809 | A1* | 9/2003 | Hall et al. ..................... | 600/425 |

FOREIGN PATENT DOCUMENTS

DE        102 10 646  A1    10/2003

* cited by examiner

*Primary Examiner* — Daniel G Mariam
*Assistant Examiner* — Nancy Bitar

(57) ABSTRACT

The invention relates to a method and a device for the combined representation of a series of 2D fluoroscopic images of the beating heart with a static 3D image data set of the same heart. The fluoroscopic images are registered with the 3D image data set and from this a 2D pseudo-projection on to the image plane of each fluoroscopic image generated in each case. This is then represented with the associated fluoroscopic image overlaid. The method is characterized in that the pseudo-projection is represented differently in each case or is not represented depending on the interval of the cardiac phase of the currently represented fluoroscopic image relative to the cardiac phase of the 3D image data set.

19 Claims, 4 Drawing Sheets

METHOD AND DEVICE FOR THE COMBINED REPRESENTATION OF 2D FLUOROSCOPIC IMAGES AND A STATIC 3D IMAGE DATA SET

CROSS REFERENCE TO RELATED APPLICATIONS

This application claims priority of German application No. 10 2006 046 733.7 filed Sep. 29, 2006, which is incorporated by reference herein in its entirety.

FIELD OF THE INVENTION

The invention relates to a method and a device for the combined representation of a series of consecutively recorded 2D fluoroscopic images of the beating heart with a static 3D image data set of the same heart.

BACKGROUND OF THE INVENTION

Minimally invasive interventions in the heart, e.g. catheter ablations and the placement of stents are nowadays generally controlled with the aid of fluoroscopic images. These are two-dimensional (2D) x-ray images recorded in real time, which are preferably obtained by means of special interventional C-arm x-ray devices. Being radioscopic images, the fluoroscopic images show no spatial-depth information, but they are available in real time and minimize the radiation loading for patient and doctor.

The idea is already emerging of supplementing the missing spatial-depth information by registering a pre-operatively recorded three-dimensional (3D) image data set of the heart with the two-dimensional fluoroscopic images and then representing the images in combination with one another, that is e.g. overlaid. The pre-operative 3D-image data set can be obtained by means of computer tomography (CT), magnetic resonance tomography (MR) or by means of 3D angiography e.g. by means of a rotational pass with a C-arm x-ray device. The combination of 2D and 3D images registered with one another then allows the doctor to obtain better orientation in the image volume.

Such a method is known from DE 102 10 646 A1. Here, a method is described for the combined representation of a series of consecutively recorded 2D fluoroscopic images of the heart, multiple 3D image data sets being recorded ECG-triggered and assigned to the corresponding 2D fluoroscopic images using the ECO. A reconstructed image of the 3D image data set is overlaid with the corresponding 2D radioscopic image and represented on a monitor.

Furthermore, DE 102 10 646 A1 also discloses a corresponding examination device, which allows registration of the 3D reconstructed images with the 2D radioscopic images by means of an image-processing apparatus.

When combining images in such a way, there are essentially two problems to be solved:

1. The Image Registration:

It must firstly be determined from which direction the 3D image volume has to be projected in order that it can be matched to the 2D fluoroscopic image. Registration is thus the determination of a transformation matrix by means of which, from the position of a voxel in the 3D image data set, the position of the voxel on the corresponding 2D fluoroscopic image can be calculated. There are various approaches to this, which will not, however, be described in detail here. Normally, various projections of the 3D image data set are calculated and compared with the 2D fluoroscopic images until a match is attained. Registration is simplified if the 3D image data set has been reconstructed from x-ray images of a rotational pass which was recorded on the same C-arm x-ray device as the fluoroscopic images. In this case, the registration can be calculated from the known equipment geometry.

2. Visualization:

The second problem is visualization of the 2D and 3D images registered with one another, i.e. the combined representation of fluoroscopic image and a corresponding projection of the 3D image data set.

The standard method of visualization is the so-called "overlay" i.e. the two images are placed over one another and made partially transparent so that they are fused with one another. This corresponds to a representation like that produced by two slide images projected onto the same screen. The proportion of the fused image that each of the two individual images makes up can be adjusted ("blending").

This has the advantage that spatially associated image information from the 2D and 3D images is also represented visually in the same position. The disadvantage is that a static 3D image data set is overlaid with a dynamic 2D image. The acquisition of a 3D image data set is namely usually ECG-triggered at a defined cardiac phase, whereas fluoroscopic images are recorded in real time, and so are not ECG-triggered. This hampers orientation above all in the cardiac phases in which the 2D image does not coincide with the 3D image.

SUMMARY OF THE INVENTION

The object of the invention is therefore to provide an improved method and a corresponding device for the combined visualization of fluoroscopic images with a static 3D image data set, which do not exhibit this disadvantage.

This object is achieved by the invention in the features of the independent claims. Preferred embodiments are specified in the subclaims.

The method according to the invention comprises the following steps: a) provision of a static 3D image data set of the heart, which has been recorded ECG-triggered at a first cardiac phase; b) acquisition, at even time intervals, of a series of 2D fluoroscopic images of the beating heart, an ECG of the beating heart being recorded during the acquisition and a cardiac phase being assigned to each fluoroscopic image; c) following acquisition of each fluoroscopic image, this fluoroscopic image being, if necessary, registered with the 3D image data set and a 2D pseudo-projection of the 3D image data set on to the image plane of the fluoroscopic image being calculated; d) representation of the series of fluoroscopic images consecutively on a screen, each fluoroscopic image being overlaid with the associated pseudo-projection. The method is characterized in that the pseudo-projection in step d) is represented differently or is not represented depending on the interval of the cardiac phase of the currently represented fluoroscopic image relative to the first cardiac phase. The pseudo-projection from the 3D image data set is thus not constant and statically blended but dynamically, depending on the cardiac phase of the fluoroscopic image currently being shown or its interval relative to the cardiac phase in which the 3D image volume was recorded. The visual impression of the combined representation can be improved by this means.

"Cardiac phase" is understood to mean a defined point in time within the cardiac cycle. The cardiac phase of the fluoroscopic images is determined according to step b) using an ECG. The 3D image data set is triggered at a first cardiac phase, e.g. the end-diastolic rest phase, and thus shows the heart during this cardiac phase.

In accordance with step c) each fluoroscopic image is registered, if necessary, with the 3D image data set. A registration is necessary e.g. if the C-arm with which the fluoroscopic image was recorded has previously moved, or if the patient has moved. If, however, multiple fluoroscopic images are recorded at the same angulation, the later images no longer have to be registered, and the registration of the first image can be adopted for the later images. Registration of the fluoroscopic image with the 3D image data set can be carried out in any manner, e.g. through calculation from the known equipment geometry, or through comparison of projections calculated from the 3D image data set with the fluoroscopic image.

"Pseudo-projection" refers to any type of representation of the 3D image data set which allows a comparison with a 2D radioscopic image (the fluoroscopic image) of the same image volume. In particular, this can be a calculated projection, the direction of projection in the calculation corresponding at least approximately to the direction of projection of the fluoroscopic image. In addition, the pseudo-projection may, however, also include only extracted edges or segmented vessels or the like, which have been determined from a calculated projection of the 3D image data set.

In a particularly preferred embodiment, the pseudo-projection is a representation generated by rendering the 3D) image data set. "Rendering" is understood to mean the representation of objects in a 3D) image data set in a computer-simulated perspective representation. For this purpose, the objects (e.g. the heart) from the 3D image data set can be segmented, for example. Using a virtual light incidence, shadows, etc. are then calculated and represented. Such an image is also referred in the context of this application as a "pseudo-projection".

Finally, the pseudo-projection can also be a sectional image through the 3D image data set perpendicular to the direction of projection of the associated fluoroscopic image. Care should be taken here to ensure that the sectional image contains an area of interest of the object represented, namely of the heart. The precise representation of the 3D image data set (projection, rendering, sectional images, clip planes, contours, extracted edges or other graphics elements etc.) is, however, immaterial to the method described here; all types of representation are possible.

Various exemplary embodiments can be used in the overlaid representation. According to a first embodiment, the transparency of the pseudo-projection which is represented overlaid over the fluoroscopic image changes. That is, when the degree of transparency of the pseudo-projection is high, the fluoroscopic image shines through strongly, when the degree of transparency is low, the fluoroscopic image is overlaid more strongly by the pseudo-projection. Where the cardiac phase of the fluoroscopic image matches that in which the 3D image data set was recorded then the pseudo-projection of the 3D image is least transparent. As the cardiac phase in the fluoroscopic image changes, the pseudo-projection becomes increasingly transparent and finally disappears completely. When the matching cardiac phase is again reached, the pseudo-projection of the 3D image data set fades in again. As the heart beats, a fading in and out of the pseudo-projection of the 3D image data set can thus be seen.

According to a second embodiment, the pseudo-projection is represented with different degrees of brightness in each case, depending on the cardiac phase of the currently represented fluoroscopic image, and is represented most brightly when the cardiac phase of the current fluoroscopic image matches the first cardiac phase in which the 3D image data set was recorded.

According to a third embodiment, the color of the pseudo-projection changes in each case, depending on the cardiac phase of the currently represented fluoroscopic image. For example, the pseudo-projection is represented in an easily visible color, e.g. red or yellow, when the cardiac phase of the current fluoroscopic image matches the cardiac phase of the 3D image data set. As the interval of the cardiac phase of the current fluoroscopic image from the first cardiac phase increases, the color changes, e.g. to green, gray or blue, i.e. to a less radiant color. Any other type of color coding of the interval of the cardiac phase of the current fluoroscopic image relative to the first cardiac phase is also possible.

These are, however, only examples. Any other appropriate change of the pseudo-projection overlaid with the fluoroscopic image that shows the doctor whether the current 2D fluoroscopic image and the 3D image data set are located in similar or different cardiac phases is possible.

Advantageously, each fluoroscopic image is represented on the screen directly after the calculation of the pseudo-projection in step c) such that steps b) to d) are essentially carried out in real time. "In real time" means that the recorded fluoroscopic images are represented so soon after the recording that the doctor can control his intervention with the aid of the image series—as on a video screen. Typically, 5-60, preferably 20-30 fluoroscopic images per second are recorded and represented on the screen with a delay of 50-1000 ms. Preferably, therefore, not just a series of fluoroscopic images is recorded, and this later represented on the screen, but the fluoroscopic images are already being represented during the recording of further images.

Besides the series of fluoroscopic images with the inventively overlaid pseudo-projection, a colored bar which, depending on the interval of the cardiac phase of the currently represented fluoroscopic image relative to the first cardiac phase, exhibits different colors or shades, is preferably also represented on the screen. This colored bar can be represented next to or in the overlaid image. The color coding indicates whether the current cardiac phase is located close to or further from the first cardiac phase. For example, green stands for the current cardiac phase being located in a predefined interval around the first cardiac phase and red for the current cardiac phase being located outside the predefined interval. This also makes it simpler for the doctor to find his/her way around the representation.

According to a further preferred embodiment, the interval of the current cardiac phase relative to the first cardiac phase is also output by an acoustic signal. This may, for example, be the modulation of a continuous tone or the intermittent output of a signal tone which always sounds once the current cardiac phase falls within a predefined interval around the first cardiac phase, or within a predefined interval outside the first cardiac phase.

The invention is also directed toward a device which is preferably suitable for executing the above-described method and comprises the following: an x-ray device which is suitable for acquiring at even time intervals a series of 2D fluoroscopic images of the beating heart; an ECG device which is suitable for recording an ECG of the beating heart during the acquisition of the fluoroscopic images such that a cardiac phase can be assigned to each fluoroscopic image, a data memory in which a static 3D image data set of the heart is stored, which data set was recorded ECG-triggered at a first cardiac phase; a computing module which is suitable for registering each of the fluoroscopic images with the 3D image data set and for generating for each fluoroscopic image a 2D pseudo-projection of the 3D image data set on to the image plane of each fluoroscopic image; a screen which is suitable for representing the series of fluoroscopic images consecutively, the associated pseudo-projection being overlaid in each case with the current fluoroscopic image. The device is characterized in that the pseudo-projection is represented on the screen differently in each case, depending on the interval of the cardiac phase of the currently represented fluoroscopic image relative to the first cardiac phase.

BRIEF DESCRIPTION OF THE DRAWINGS

The invention will now be described in detail using exemplary embodiments with reference to the accompanying drawings, in which.

DETAILED DESCRIPTION OF THE INVENTION

Figure 1:
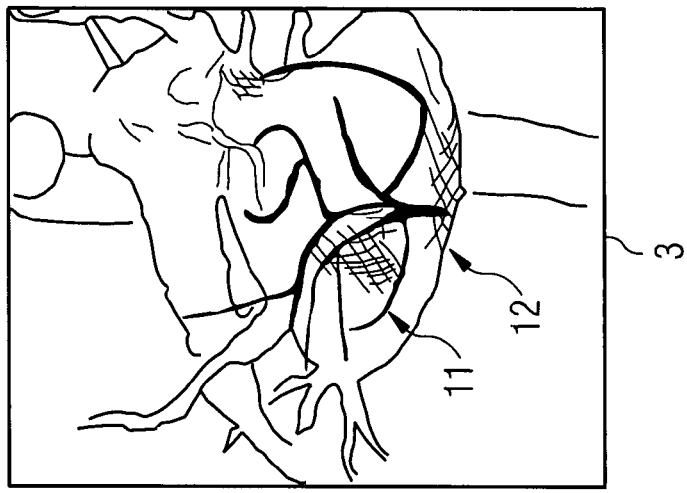
FIG. 1 shows a schematic representation of a fluoroscopic image of the heart.

FIG. 1 shows in a simplified manner a fluoroscopic image 1 of the beating heart with a vascular tree 11. A good representation of a vascular tree 11 can in particular be achieved through the administration of contrast means. FIG. 1 reproduces only a single fluoroscopic image 1, whereas during an intervention in the heart a series of fluoroscopic images 1 comprising approximately 1-10, preferably 2-5, images per second, will typically be recorded. On this series of images, the vascular tree 11 would move accordingly with the heartbeat.

Figure 2:
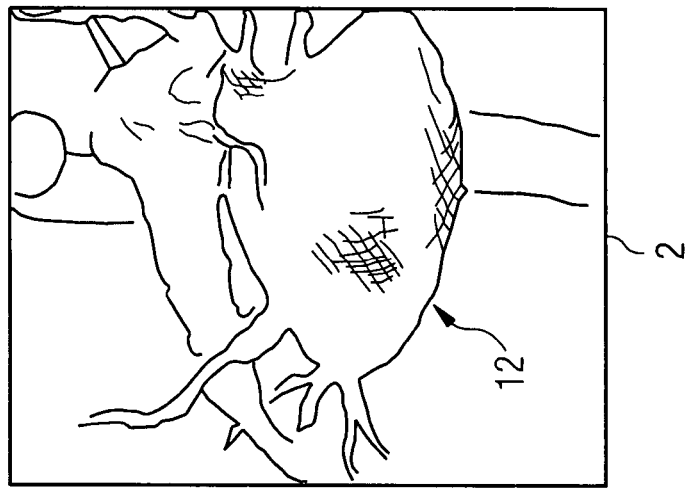
FIG. 2 shows a schematic representation of a pseudo-projection of a 3D image data set of the same heart shown in FIG. 1.

FIG. 2 shows the same object as FIG. 1, but in a different representation. FIG. 2 is actually designed to reproduce the impression of a pseudo-projection of a 3D image data set of the same heart obtained by means of rendering. The 3D image data set was produced e.g. by means of MR, CT or 3D rotational angiography and consequently exhibits spatial resolution and depth information. The heart 12 and some supplying vessels as well as the aorta can be recognized in perspective. However, several minutes are needed in order to acquire such a 3D image data set, which is why this has to be recorded pre-operatively.

Figure 3:
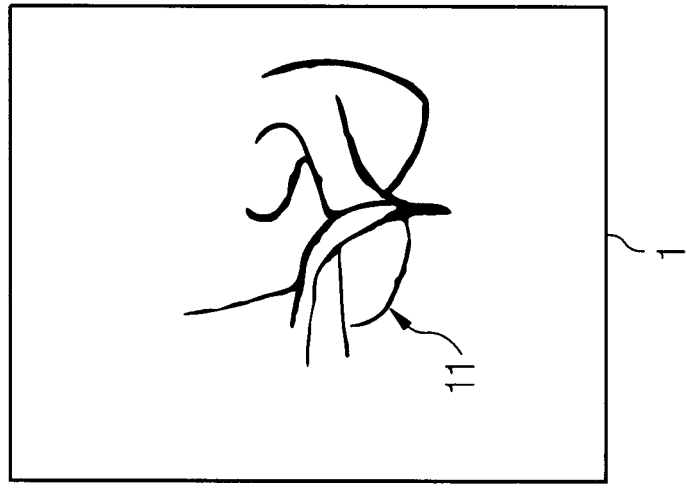
FIG. 3 shows a fusion of the representations shown in FIGS. 1 and 2.

FIG. 3 now shows a fusion 3 of images 1 and 2, as has been carried out conventionally, namely by simple overlaying the current fluoroscopic image 1 in each case with the pseudo-projection 2. Bot the vascular tree 11 and the heart 12 can be recognized on the image, however, the vascular tree 11 moves with the heartbeat, while the heart 12 remains static. This highlights the problem of the invention, namely that fusion allows orientation in the 3D image data set only for certain cardiac phases of the fluoroscopic images 1.

Figure 4:
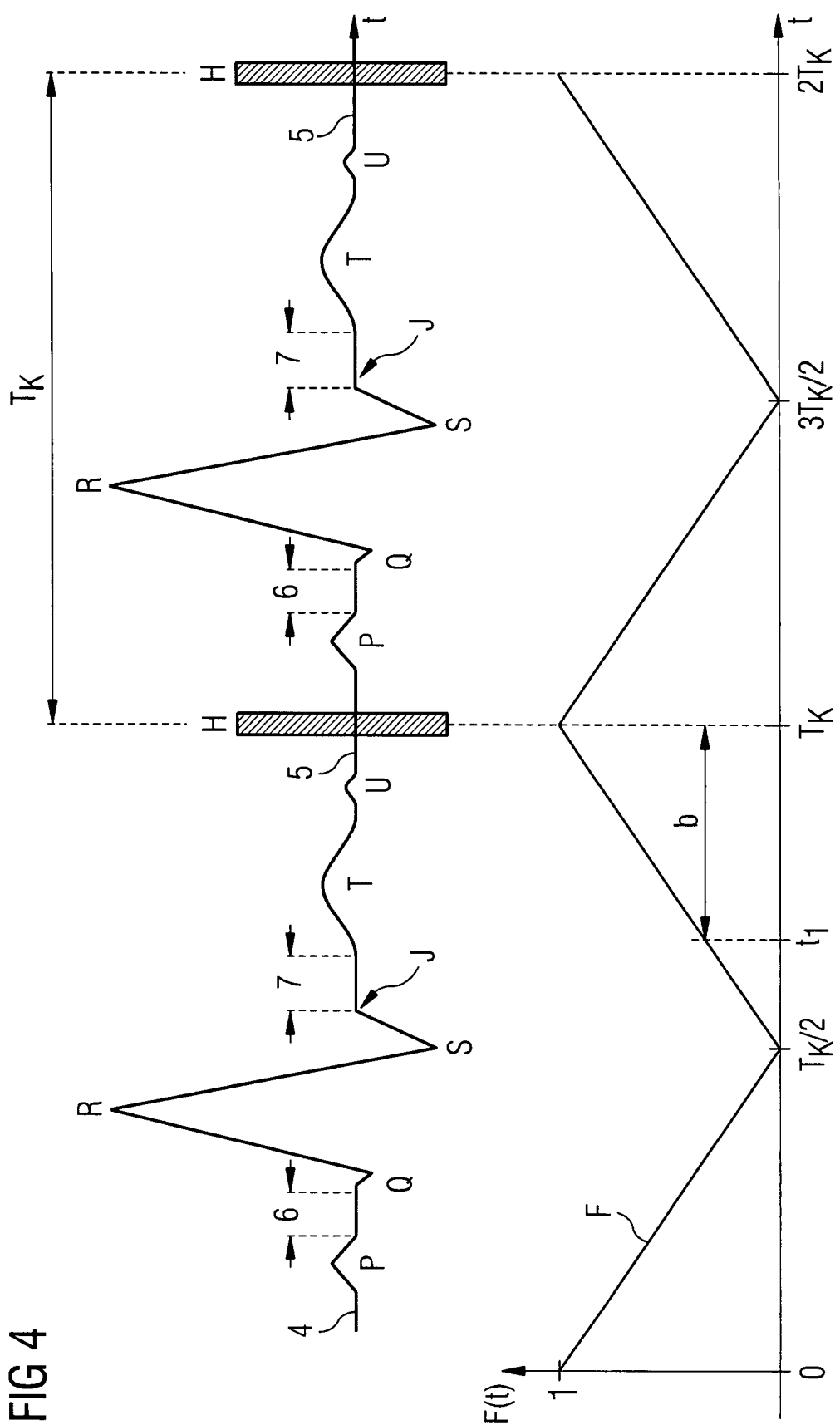
FIG. 4 shows a graph of an ECG signal and of a function F against time t that determines the representation of the pseudo-projection.

In the top of FIG. 4, an ECG signal 4 is reproduced which was recorded during acquisition of the fluoroscopic images 1. Two cardiac cycles $T_K$ are represented which each show the QRS complex, as well as the P wave, the J point the U wave and the T area. A gray bar marks in each case the point in time H which lies within the cardiac rest phase 5 in the end diastole. In the example shown, a 3D image data set which was triggered at the time H is worked with. Alternatively, the trigger time H could also be set in the PR segment 6 or the ST segment 7, in which the heart is likewise located in a relatively reproducible position. It is important that the images for the 3D image data set are in each case acquired at the same point of time within the cardiac cycle.

Below that, a function F(t) is plotted against time t. The function F(t) describes for example the intensity with which the pseudo-projection 2 of the 3D image data set is fused with the fluoroscopic images 1 (for example the brightness). In the first cardiac phases H, F(t) has a value of 1, which declines in a linear manner to 0 at the center of the cardiac cycle between two times H. The time $T_1$ has, for example, the interval marked b relative to the cardiac phase H, at which interval F(t) has a value of approximately 0.4. The function F(t) thus represents a brightness or transparency value factor with which the pseudo-projection of the 3D image data set is represented. The brightness or color of the pseudo-projection 2 which is overlaid with the current fluoroscopic image 1 decreases or increases in a linear manner in each case, according to the function F(t) that is shown by way of example.

If the interval between two cardiac phases H is designated $T_K$ (duration of a cardiac cycle), the function F(t) can be expressed by $$F(t) = |2(t/T_K \bmod 1) - 1|$$

where mod designates the modulus function. The function F(t) is always positive as an image cannot be faded in with negative intensity or brightness.

It should be noted here that the duration of a cardiac cycle $T_K$ is not constant. The function F(t) must therefore in each case be recalculated using an averaged $T_K$ or using the duration of the last cardiac cycle.

Figure 5:
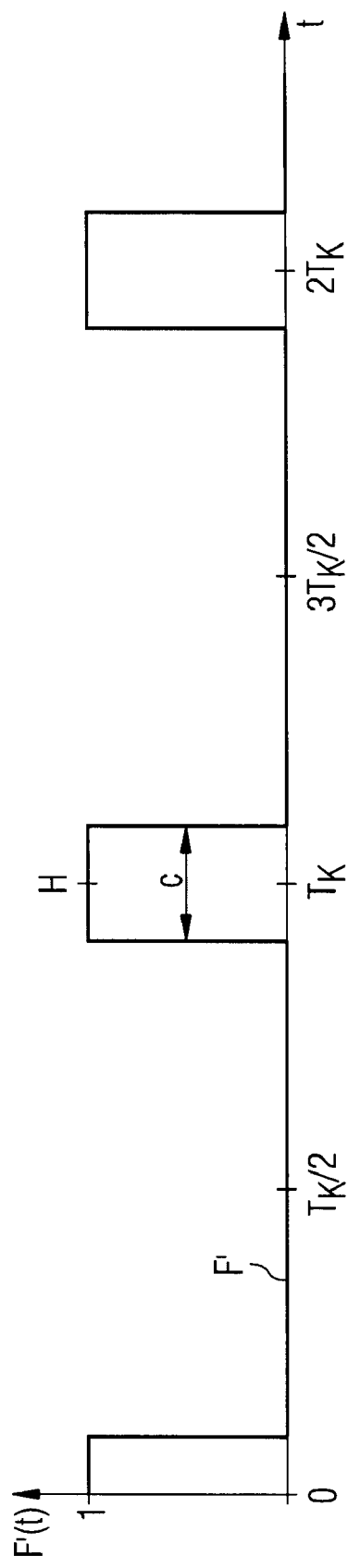
FIG. 5 shows a graph of an alternative function F' that determines the representation of the pseudo-projection.

FIG. 5 shows an alternative function F'(t) which determines the color or brightness of the pseudo-projection 2. The function F'(t) does not exhibit continuous transitions but has the value 1 in all interval c around the cardiac phase U and the value 0 outside this interval. This function means therefore that the pseudo-projection 2 is in each case fully faded in a time interval c about the first cardiac phase H, and is not represented at all during the other cardiac phases. This has the advantage that the electrophysiologist will not be confused by the representation of a pseudo-projection 2 that shows the heart in a completely different movement status from the current fluoroscopic image 1.

Figure 6:
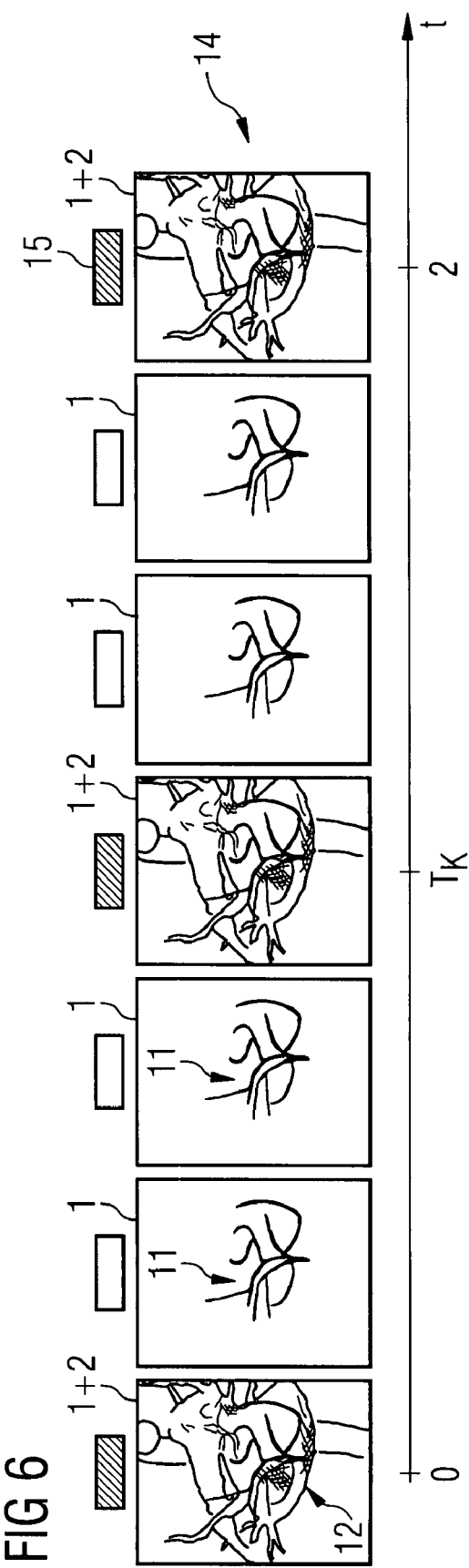
FIG. 6 shows a representation of a time series of fluoroscopic images with overlaid, differently represented, pseudo-projections.

FIG. 6 shows an example of a time series 14 of fluoroscopic images 1 which in each case are overlaid with a pseudo-projection image 2 of the 3D image data set in accordance with the function F'(t). For the sake of simplicity, the fluoroscopic images 1 in the drawing are in each case shown with an identical vascular tree 11, whereas in reality this vascular tree 11 would of course move with the heartbeat and consequently shift slightly from image to image. On the first, fourth and seventh images, a pseudo-projection 2 of the whole heart which was calculated from the static 3D image data set is also faded in each case, in addition to the vascular tree 11. This fading in thus takes place in accordance with F'(t) within the time intervals c around the first cardiac phases H (that is, at the times 0, $T_K$, $2T_K$ etc.).

According to yet another alternative embodiment, the function that determines the representation of the pseudo-projection 2 of the 3D image data set can also comprise a non-linear, curvilinear function, e.g.

$$F'''(t) = |\cos(t\pi/T_k)|.$$

FIG. 6 shows yet a further optional feature, namely a colored bar 15, which, depending on the cardiac phase of the currently represented fluoroscopic image 1, and consequently, depending on the representation or non-representation of the pseudo-projection 2, changes its color. In the example shown, the colored bar 15 has on a dark shade in each case when the pseudo-projection 2 is fused with the current fluoroscopic image 1.

Figure 7:
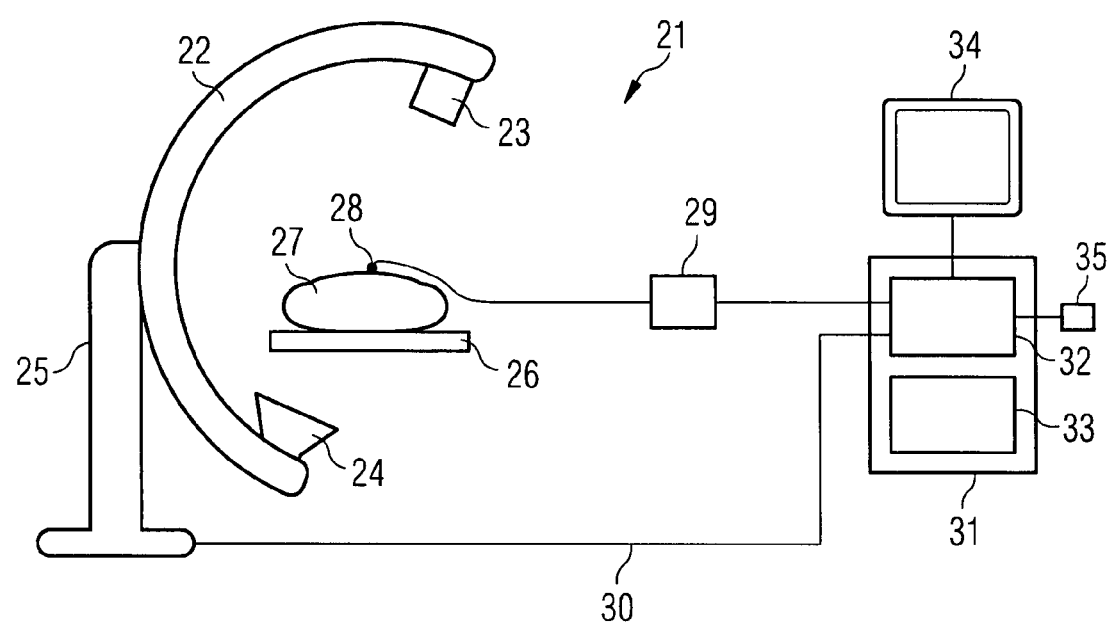
FIG. 7 shows a schematic representation of an exemplary embodiment of the device according to the invention.

Finally, FIG. 7 shows an exemplary embodiment of a device 21 according to the invention. This comprises a C-arm x-ray device with a C-arm 22, on the ends of which an x-ray source 23 and an x-ray detector 24 are arranged. The C-arm is movably mounted on a stand 25, and can thus be displaced about a patient bed 26. Represented on the bed 26 is a patient 27, on whom, for example, a minimally invasive intervention in the heart, for example a catheter ablation or a balloon dilatation, is to be carried out. For this purpose, an ECG signal, which is forwarded to the ECG device 29, is recorded simultaneously with the electrodes 28. The evaluation of the ECG signal and of the x-ray images (fluoroscopic images) recorded with the C-arm 22 is carried out by means of the evaluation unit 31. This comprises in particular a computing module 32 and a data memory 33. The image data, in particular fluoroscopic images 1, recorded with the x-ray gantry 23, 24 are transmitted via a data cable 30 to the computing module 32. A 3D image data set can either be recorded likewise with the C-arm, namely in a rotational pass as part of a 3D rotational angiography, or it is generated by means of a different imaging system such as MR or CT and stored in the data memory 33. The computing module 32 is responsible for the registration of the current fluoroscopic images 1 with the 3D image data set and controls the overlaid representation on the screen 34.

The series of images 14 represented in FIG. 6 can thus, for example, be represented in real time on the screen 34. A loudspeaker 35 is optionally also connected to the evaluation unit 31, which according to the embodiment described hereinabove emits an acoustic signal when the cardiac phase of the current fluoroscopic image 1 is located within a predetermined interval around the first cardiac phase H.

Thus, using the method described and the device described when "overlaying" a 3D image data set of the heart with 2D fluoroscopic recordings 1, the type of fusion can be made dependent upon the status of the cardiac cycle of the 2D fluoroscopic image, and the visual impression of the overlay can thereby be improved.

The invention claimed is:

1. A method for combining a representation of a 2D fluoroscopic image of a beating heart of a patient with a static 3D image data set of the beating heart, comprising:
   recording the static 3D image data set of the heart triggered by ECG at a first cardiac phase;
   acquiring the 2D fluoroscopic image of the beating heart;
   stimulatingly recording an ECG of the beating heart during the acquisition and assigning a cardiac phase to the 2D fluoroscopic image;
   calculating a 2D pseudo-projection of the 3D image data set on to an image plane of the fluoroscopic image;
   and representing the 2D fluoroscopic image on a screen overlaid with the 2D pseudo-projection, wherein the 2D pseudo-projection is represented differently on the screen depending on an interval of the cardiac phase of the 2D fluoroscopic image relative to the first cardiac phase; wherein a series of 2D fluoroscopic images of the beating heart are consecutively recorded at even time intervals and each 2D fluoroscopic image is assigned an associated cardiac phrase, wherein a plurality of 2D pseudo-projections of the 3D image data set are calculated for each 2D fluoroscopic image on to an image plane of each 2D fluoroscopic image, and wherein the 2D fluoroscopic images are consecutively represent on a screen and each 2D fluoroscopic image is overlaid with an associated 2D pseudo-projection corresponding to a currently represented 2D fluoroscopic image, and wherein the associated 2D pseudo-projection is represented differently on the screen depending on an interval of a cardiac phase of the currently represented 2D fluoroscopic image relative to the first cardiac phase or is not represented during other cardiac phases.

2. The method as claimed in claim 1, wherein the 2D fluoroscopic image is registered with the 3D image data set.

3. The method as claimed in claim 1, wherein the 2D pseudo-projection is represented with differing transparency depending on the interval of the cardiac phase of the 2D fluoroscopic image relative to the first cardiac phase and a least transparent is represented when the cardiac phase of the 2D fluoroscopic image matches the first cardiac phase.

4. The method as claimed in claim 1, wherein the 2D pseudo-projection is represented with differing brightness depending on the interval of the cardiac phase of the 2D fluoroscopic image relative to the first cardiac phase and a brightest is presented when the cardiac phase of the 2D fluoroscopic image matches the first cardiac phase.

5. The method as claimed in claim 1, wherein the 2D pseudo-projection is represented in different colors depending on the interval of the cardiac phase of the 2D fluoroscopic image relative to the first cardiac phase.

6. The method as claimed in claim 1, wherein the fluoroscopic image is represented on the screen directly after the calculation of the 2D pseudo-projection so that the presentation is carried out in real time.

7. The method as claimed in claim 1, wherein a colored bar which exhibits different colors depending on the interval of the cardiac phase of the currently represented fluoroscopic image relative to the first cardiac phase is represented on the screen.

8. The method as claimed in claim 1, wherein an acoustic signal is output which indicates the interval of the cardiac phase of the currently represented fluoroscopic image relative to the first cardiac phase.

9. The method as claimed in claim 1, wherein the 2D pseudo-projection is a calculated projection of the 3D image data set in a direction of projection of the 2D fluoroscopic image.

10. The method as claimed in claim 1, wherein the 2D pseudo-projection is a representation of edges or segments extracted from a calculated projection of the 3D image data set.

11. The method as claimed in claim 1, wherein the 2D pseudo-projection is a representation generated through rendering the 3D image data set.

12. The method as claimed in claim 1, wherein the 2D pseudo-projection is a sectional image through the 3D image data set perpendicular to a direction of projection of the fluoroscopic image.

13. A device for combining representations of a series of consecutively recorded 2D fluoroscopic images of a beating heart of a patient with a static 3D image data set of the beating heart, comprising:
- an x-ray device that acquires the series of 2D fluoroscopic images of the beating heart at even time intervals;
- an ECG device that records an ECG of the beating heart during the acquisition of the fluoroscopic images so that a cardiac phase is assigned to each fluoroscopic image;
- a data memory that stores the static 3D image data set of the beating heart that is ECG-triggered recorded at a first cardiac phase;
- a computing device that registers the 2D fluoroscopic images with the 3D image data set and calculates a plurality of 2D pseudo-projections of the 3D image data set for each 2D fluoroscopic images on to an image plane of each 2D fluoroscopic image; and
- a screen that consecutively represents the 2D fluoroscopic images each overlaid with an associated 2D pseudo-projection corresponding to a currently represented 2D fluoroscopic image, wherein the associated 2D pseudo-projection is represented differently on the screen depending on an interval of a cardiac phase of the currently represented fluoroscopic image relative to the first cardiac phase.

14. The device as claimed in claim 13, wherein the 2D pseudo-projection is represented with differing transparency depending on the interval of the cardiac phase of the currently represented 2D fluoroscopic image relative to the first cardiac phase and a least transparent is represented when the cardiac phase of the currently represented 2D fluoroscopic image matches the first cardiac phase.

15. The device as claimed in claim 13, wherein the 2D pseudo-projection is represented with differing brightness depending on the interval of the cardiac phase of the currently represented 2D fluoroscopic image relative to the first cardiac phase and a brightest is presented when the cardiac phase of the currently represented 2D fluoroscopic image matches the first cardiac phase.

16. The device as claimed in claim 13, wherein the 2D pseudo-projection is represented in different colors depending on the interval of the cardiac phase of the currently represented 2D fluoroscopic image relative to the first cardiac phase.

17. The device as claimed in claim 13, wherein each fluoroscopic image is represented on the screen directly after the calculation of the 2D pseudo-projection so that the presentation is carried out in real time.

18. The device as claimed in claim 13, wherein a colored bar which exhibits different colors depending on the interval of the cardiac phase of the currently represented fluoroscopic image relative to the first cardiac phase is represented on the screen.

19. The device as claimed in claim 13, wherein an acoustic signal is output which indicates the interval of the cardiac phase of the currently represented fluoroscopic image relative to the first cardiac phase.

* * * * *